United States Patent [19]
Fay et al.

[11] Patent Number: 5,789,676
[45] Date of Patent: Aug. 4, 1998

[54] SETTLING PROCESS ANALYSIS DEVICE AND METHOD

[75] Inventors: Charles Robert Fay, Stratford, Conn.; Ralph W. Barnes; Harold Leon Robinson, both of Winston-Salem, N.C.

[73] Assignee: Cytec Technology Corp., Wilmington, Del.

[21] Appl. No.: 717,876

[22] Filed: Sep. 23, 1996

Related U.S. Application Data

[63] Continuation-in-part of Ser. No. 233,178, Apr. 26, 1994, Pat. No. 5,635,632.
[51] Int. Cl.$^6$ .................................................. G01N 15/06
[52] U.S. Cl. ............................... 73/290 V; 73/61.63
[58] Field of Search ........................ 73/61.65, 61.63, 73/61.75, 270 V, 1.83, 64.42; 364/509

[56] References Cited

U.S. PATENT DOCUMENTS

| | | | |
|---|---|---|---|
| 4,014,650 | 3/1977 | Sigelmann | 73/64.01 |
| 4,528,842 | 7/1985 | Brown | 73/61.75 |
| 5,125,264 | 6/1992 | Beuzard | 73/61.75 |

*Primary Examiner*—Christine K. Oda
*Attorney, Agent, or Firm*—Joseph J. Mallon; Frank M. Van Riet

[57] ABSTRACT

A system and method for monitoring the dynamics of particle motion in a liquid-solid media including the rate of settling of particles, the identification of unsettled particle clouds, and the identification and control of the bed level of settled particles in a slurry within a settler. The system includes an ultrasound transducer and a receiver for detecting echoes from particles in the slurry. The echoes are processed to determine the bed level of the settled particles, the position of unsettled particle clouds, and the rate of settling of the particle clouds, employing a neural network preferably with a Fuzzy Logic controller.

6 Claims, 5 Drawing Sheets

SETTLING PROCESS ANALYSIS DEVICE AND METHOD

This is a continuation-in-part of application Ser. No. 08/233,178 filed Apr. 26, 1994, U.S. Pat. No. 5,635,632.

BACKGROUND OF THE INVENTION

Accurate determination of the bed level of settled particles is important to control settling tanks such as clarifiers, thickeners, and aluminum and coal settlers. During operation of a settler, a slurry formed of a liquid laden with particles such as aluminum, solid wastes or coal is carried via a pipe to the center top, i.e., the "center well" of a settling tank. The slurry then is discharged into the center well, and the particles are allowed to settle onto the bottom of the tank. The settled particles form a bed, and the liquid-solid interface between the waste suspension and the liquid above is the bed level. Often, however, the particles in the slurry do not immediately settle to the bottom, but remain suspended in the tank to form a "cloud" that can create or be a predictor of an upset condition. Knowledge of the location of bed level and/or cloud dimensions and intensity is important for controlling the amount of chemicals or flocculants added to the tank to control the settling process.

Settling rates in thickeners and clarifiers have been manually controlled due to lack of reliable measurement instrumentation. Settling rates have been determined manually by depositing a sample of the slurry taken from the settling tank into a graduated cylinder, and employing photo cells or visual observation to measure the time for the suspended particles to fall a given distance within the cylinder. This method, although simple and inexpensive, is not a reliable means of measuring settling rates since it depends on obtaining a representative sample from the settler, is performed outside the settler, and its accuracy depends upon a human observer.

The bed level of settled particles also has been determined by using simple noncoherent fish finder (A-Mode) ultrasound systems. In an A-mode system, a transducer sends an ultrasound pulse into the particle suspension contained in a "settler". Low level echoes return from the surface of the settled bed. If the speed of the ultrasound pulse is known, then the distance to the bed level of settled particles can be calculated from the time between the transmitted pulse and the returned echo by using the well known range equation:

$$d = ct/2$$

where d=distance to the target, c=speed of sound in the liquid or other media t=round trip time from the transducer pulse to echo return.

The simple A-mode systems of the art are useful when a distinct bed level boundary exists and where that boundary is essentially perpendicular to the ultrasound transducer path. However, if the bed level boundary is not nearly perpendicular to the transducer path, or when there is no distinct bed level boundary, then echoes from the bed level may be blurred or undetectable. Moreover, in the unsettled particles where a bed level might exist, A-mode ultrasound systems provide little or no information on settler performance.

Currently, non-coherent A-mode systems cannot reliably detect bed level, cloud layer and cloud layer characteristics. A need therefore exists for reliable and accurate determination of bed level and cloud layer existence and particle activity within the cloud layer.

SUMMARY OF THE INVENTION

The invention provides a system and method for use in detection and control of the bed level of settled particles in a slurry. The invention also may be used to control the settling rate of particles in slurries. The system includes an ultrasound transducer for transmitting ultrasound pulses into a slurry within a settling tank. The system also employs a preamp-receiver to detect echoes from particles in the slurry. These echoes are processed to determine the bed level of the settled particles, the existence of clouds and the activity of particles in the cloud in the settler, as well as the settling rate of the particles. The bed level and settling rate may be used to control addition of chemicals, slurry additions and the like to the settling tank.

The system employed in the invention can operate in any of the following coherent modes: (i) the peak method (coherent A-mode) to detect the bed level when it exists, (ii) the moving target detection mode to detect particle clouds and to assess their characteristics and also to detect the bed level, and (iii) the Doppler processing mode to detect ascending and descending particle speed in the liquid suspension in the settling tank. The peak method and the moving target detection modes are called the image modes.

In another aspect, the invention provides a system and method for locating the bed level of settled particles within a liquid slurry. The methods comprise transmitting ultrasonic sound waves of a first frequency from a transducer into a slurry that has a bed of settled particles and a cloud of settling particles. The ultrasonic waves generate echoes from the bed and echoes from the settling particles. Digital and analog electrical signals are generated from the echoes, and the electrical signals are processed to characterize the bed level and the settling of the particles.

In another aspect, the invention provides a system for identifying bed level and the settling particles. The system employs a transducer for sending ultrasound signals into a slurry. The ultrasound signals are reflected as echoes which are captured by a preamp-receiver. The preamp-receiver converts the echoes to analog electrical signals. These signals are directed to individual sine and cos channels where those signals are multiplied with either sine or cos signal in a mixer and filtered to remove high frequency products of the mixer. An analog switch multiplexes the resulting new analog signals to an analog-digital converter which converts those analog signals to digital signals. The digital signals are stored in a data acquisition memory for numerical processing according to any of the peak method, moving particle method, or the Doppler method as described below. The system of the invention includes a range phase cancellation memory for storage of a time-delayed version of the background or baseline noise.

The system and method of the invention employ a wider dynamic range of echo detection than has been employed in prior art non-coherent A-mode systems. Echoes therefore can be processed to yield a broader range of amplitude and phase information, range time delay information, cloud layer activity information, as well as particle speed information, such as settling rate.

In another aspect, the system and method of the invention can be employed to monitor settler performance and conditions regardless of the presence of a detectable bed level. In yet another aspect, the system and method of the invention enables reliable detection and characterization of unsettled cloud properties such as internal particle activity and cloud thickness from the liquid level to the bottom of the settler. A multiplicity of unsettled clouds therefore can be simultaneously detected and characterized. The results can be employed as an indicator of a settler upset condition.

Having briefly summarized the invention, the invention will now be described in detail by reference to the following specification and non-limiting examples. As used herein, "settler" includes devices such as clarifiers, thickeners or other similar apparatus.

BRIEF DESCRIPTION OF THE DRAWINGS

FIGS. 1A and 1B also show plots of unipolar echo amplitude vs. depth within the settling tank.

DETAILED DESCRIPTION OF THE INVENTION

The bed level of settled particles may be defined as the level where the downward speed of settling particles is less than a given value, for example 2"/min., which is near zero speed, or where a distinct, detectable boundary exists between the unsettled particle cloud and the settled bed.

Figure 1A:
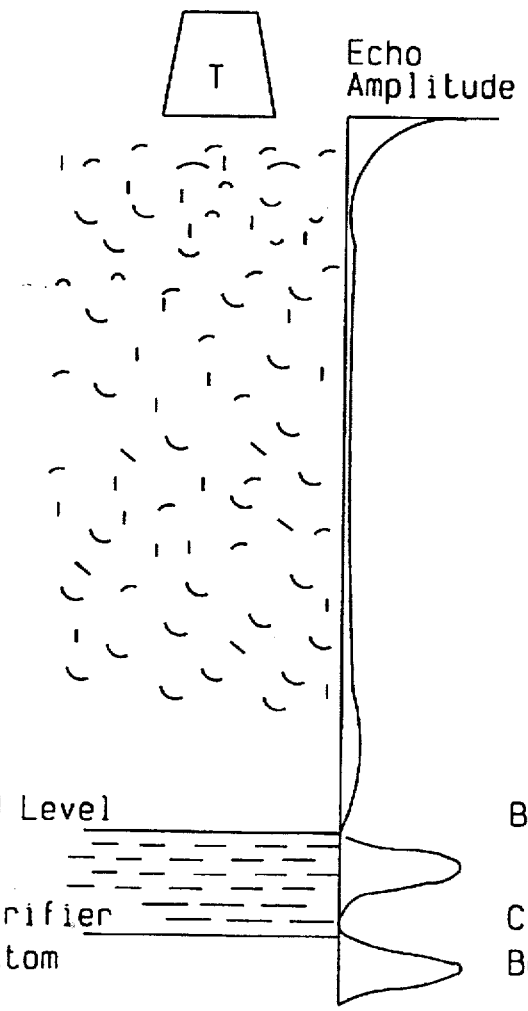
FIGS. 1A and 1B show a schematic of the technique for measurement of bed level.
Figure 1B:
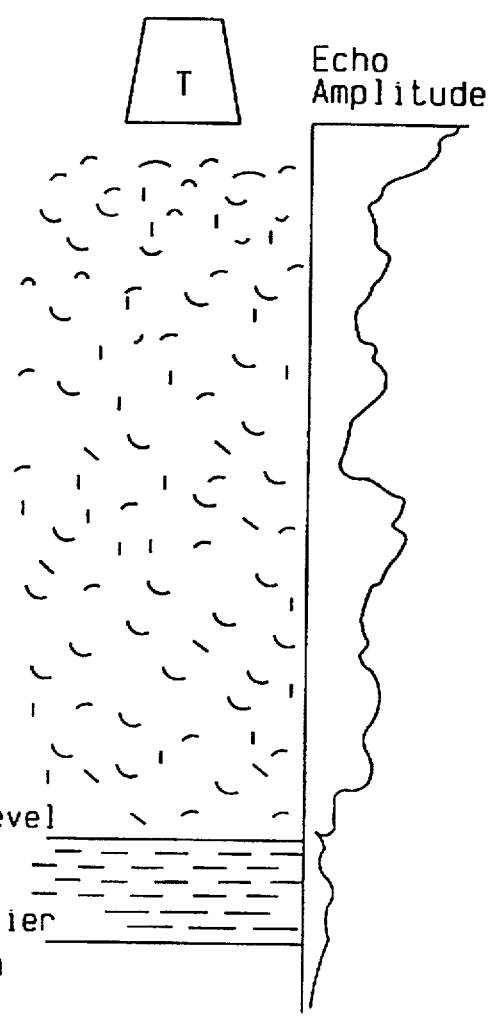

FIG. 1A shows a well defined bed level where an unsettled particle cloud is near the bottom of a settling tank but does not overlap the bed level. Echoes from the bed level therefore are clear and distinct. The amplitude of the echo signals from the bed level also are shown in FIG. 1A. In contrast, and as shown in FIG. 1B, when an unsettled particle cloud overlaps the bed level, echoes from the bed level are disrupted by echoes from the particle cloud. As a result, and as is shown in FIG. 1B, echoes from the bed level are blurred.

Figure 2A:
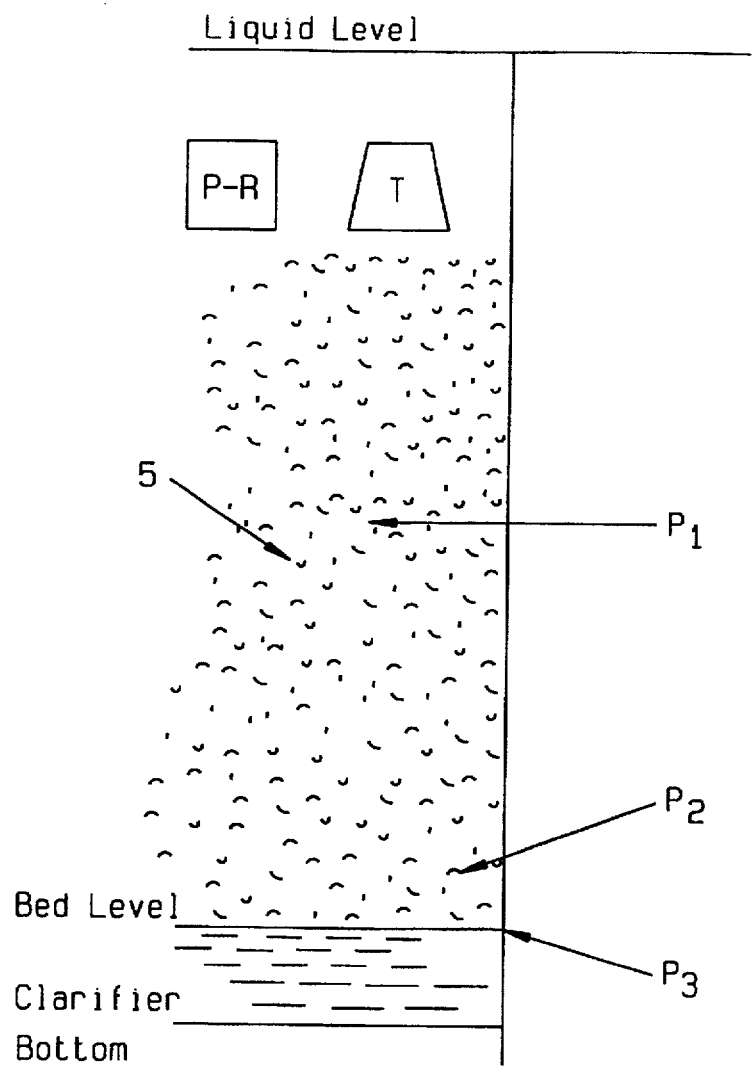
FIG. 2A shows a schematic of echo detection at various points in a slurry.

In accordance with the invention, and as shown in FIG. 2A, an ultrasound transducer T transmits an ultrasonic pulse into particle cloud 5 within a settling tank. Echoes from the particles generated by the ultrasonic pulse are reflected back toward the preamp-receiver P-R when the ultrasonic pulse encounters particle clouds, bed level or settler bottom.

Figure 2B:
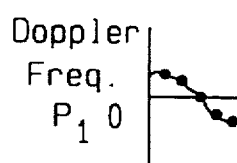
FIGS. 2B–2D represent detected echo signals at various points shown in FIG. 2A.
Figure 2C:
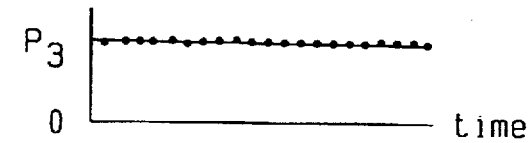
Figure 2D:
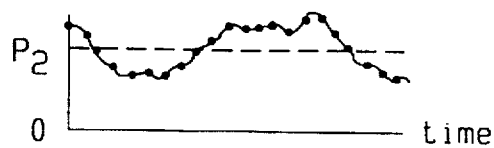

FIG. 2B–D present signals generated by the Doppler method as well as the moving particle detection method employed in the invention for points P1, P2 and P3 in FIG. 2A. Point P3 in FIG. 2A represents the settled bed level at the bottom of a settler tank. Point P2 represents a position in cloud 5 slightly above the surface of the settled bed level, and point P1 represents a position within particle cloud 5. At points P1 and P2, echo signals vary with time about a zero baseline. The rate of variance depends upon the speed of the particles, the transducer frequency and the sound speed in the slurry. Typical waveforms generated from these particles are shown in FIGS. 2B and 2D. These waveforms can be processed by known Fast Fourier Transform (FFT) in the Doppler method and the moving target detection method to locate bed level. These data are used to estimate a bed level when a distinct bed level boundary is not present. In contrast, signals from the nearly stationary bed level boundary at point P3 yield a constant or nearly constant signal as shown in FIG. 2C. The waveform in FIG. 2C, when analyzed by FFT or moving target detection mode give a zero or near zero particle speed.

Figure 3A:
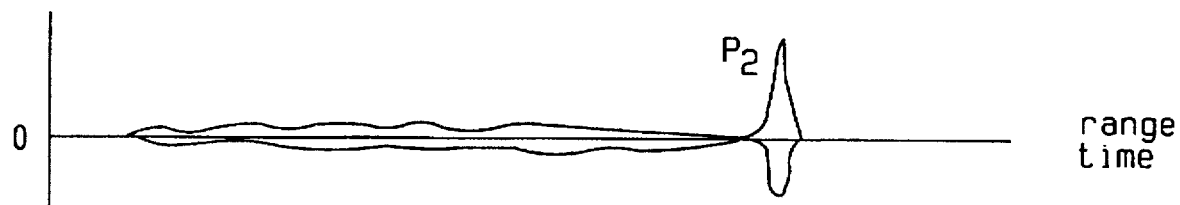
FIGS. 3A–3C show the effects of processing of echo signals by the invention.
Figure 3B:
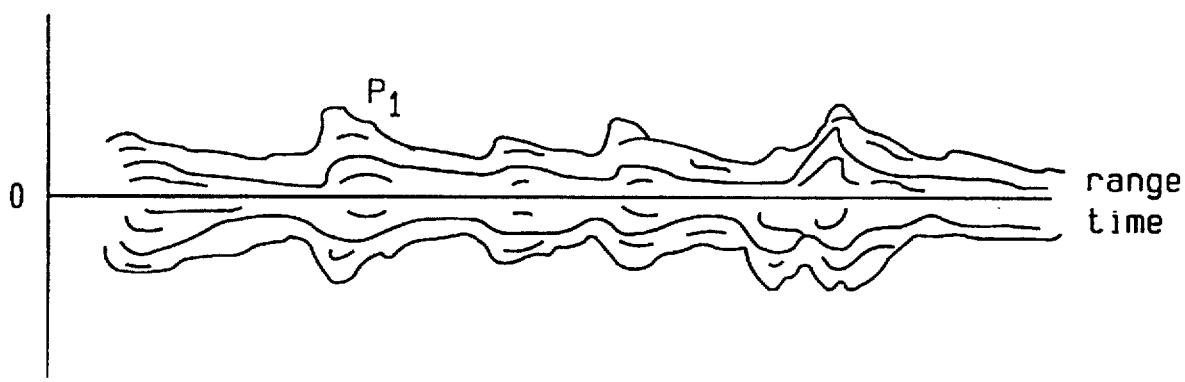
Figure 3C:
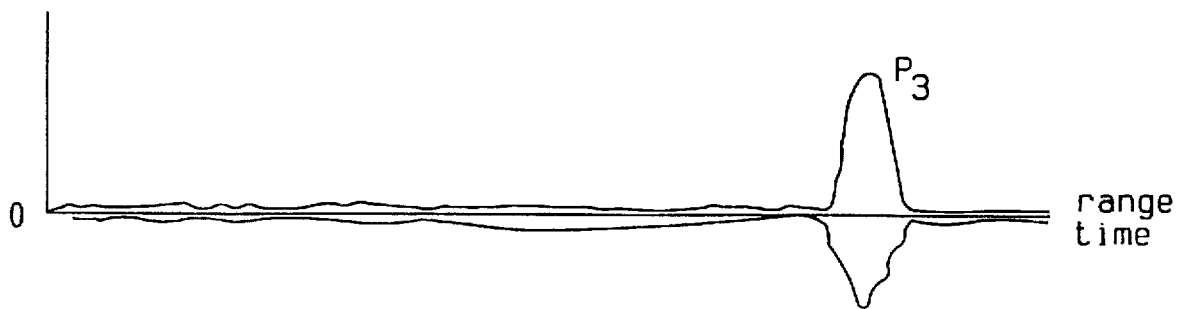

In each of the Doppler, peak and moving target coherent detection modes of the invention, sine (sin) and cosine (cos) signals are multiplied with the echo analog signals. The amplitude and the envelope of frequencies of the resulting analog signals in each of the sine and cos channels represents echo data obtained along the path of the ultrasound from the transducer. FIG. 3A shows analog signals generated by echoes from a distinct, slowly undulating bed level with no unsettled particle cloud overlapping the bed level. FIG. 3B presents amplitude and frequency of echo data obtained from an unsettled cloud layer that extends along substantially the entire transducer path to the settler bottom. FIG. 3C shows amplitude and frequency of echo data obtained from a single distinct stationary bed level. Echo amplitude data at varying depths in the tank can be calculated from the sin and cos channel data as described below.

Figure 4:
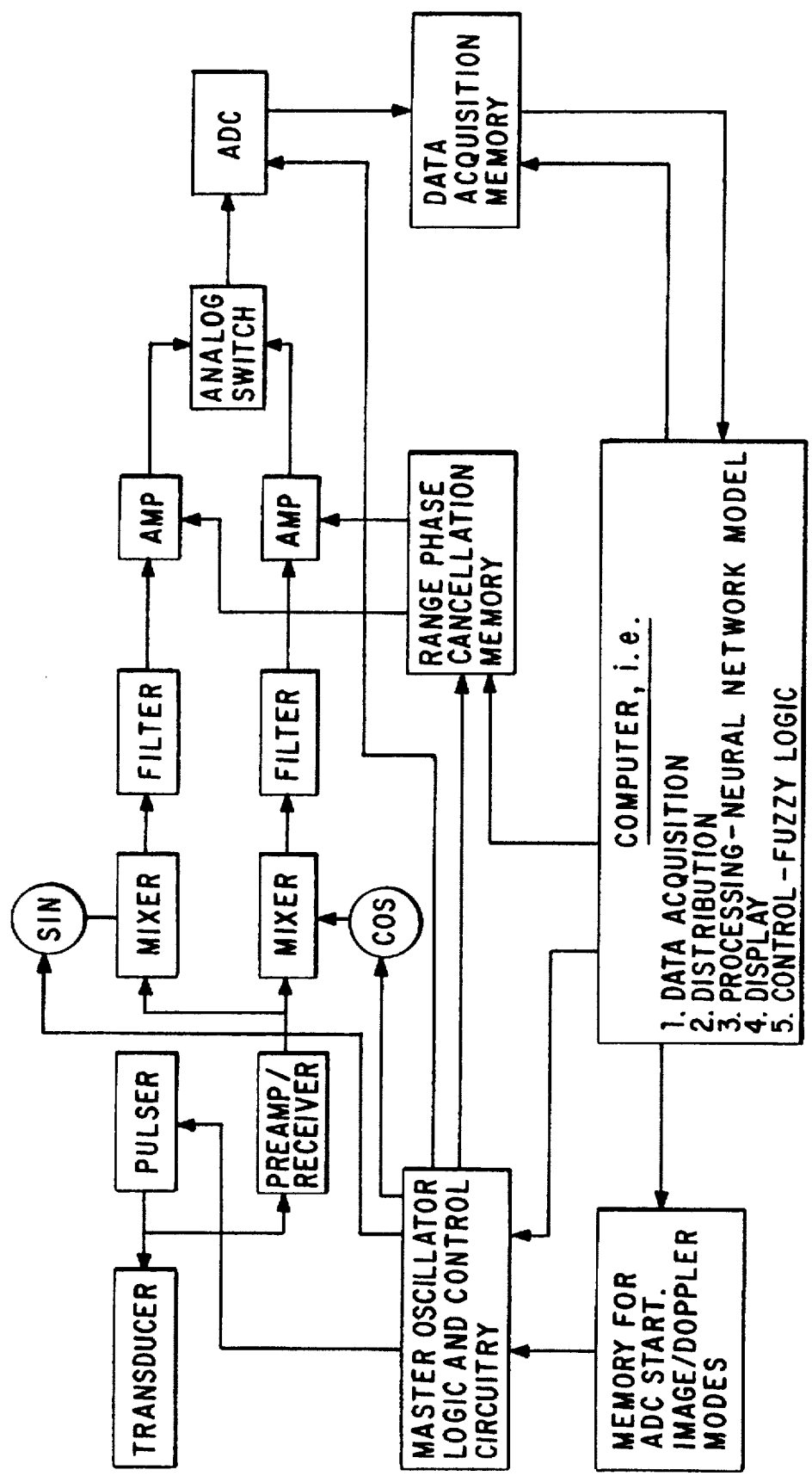
FIG. 4 is a block diagram of the system of the invention.

Referring to FIG. 4, a block diagram of the system of the invention is shown. As shown in FIG. 4, a commercially available crystal oscillator, which is an element of the master oscillator, controls the time and logic functions of the system. Useful crystal oscillators are available from Digikey Co. of Minn. A frequency resonant crystal in the master oscillator provides a stable basic frequency for the system. The master oscillator and logic also generate sin and cos frequencies for multiplying with the echo signals to generate new analog signals in the mixers. These sin and cos frequencies are coherent with the transducer ultrasound frequency and differ from each other by a 90° phase shift. A time gated sin channel pulse signal, generated by the master oscillator and amplified by the pulser, serves as the transducer excitation signal. All of these signals are coherent with the crystal oscillator. A synchronous binary counter chain (not shown but part of the master oscillator block) divides the crystal oscillator frequency to provide a desired transducer repetition frequency. For example, a transducer repetition frequency for use in a 10 ft deep settler may employ a 0.003 second delay between successive transducer pulses. The time delay permits all echoes returning from a first transducer ultrasound pulse to be received by a preamp-receiver before the next transducer pulse is transmitted.

Echo signals from the sin/cos channel mixers are filtered to remove higher order frequencies, forwarded to an amplifier, and then sent to an analog-to-digital converter (ADC) via an analog switch. The ADC alternately samples the analog signals from sine and cos channels via the analog switch for conversion into digital code. The resulting digital code is sent to the Data Acquisition Memory. All timing and logic signals to accomplish the analog switch selection, analog-to-digital conversion and storage in data acquisition memory are generated in the Master Oscillator Block, as is recognized by the art skilled. This enables the system to be synchronized with the master crystal oscillator and the system to be coherent.

Echoes are detected and amplified in the preamp-receiver block. A feature of the preamp-receiver is the provision for time gain control voltage adjustment. The time gain control voltage can be shaped to increase the preamp gain to compensate for transducer ultrasound path spreading as the ultrasound pulse travels to the settler bottom. Echo amplitudes for all targets along the transducer beam path therefore tend to be equalized, therefore providing more reliable analog echo data.

Amplified echo signals from the preamp-receiver are transmitted to sin and cos mixers where they are multiplied by the sin and cos signals from the master oscillator. The analog signal output of each mixer consists of signals with the echo amplitude having a frequency equal to the difference between the transducer excitation frequency and the returned echo frequency, plus higher frequency terms. The higher frequency terms are eliminated by filters following the mixers as shown in FIG. 4. The sin/cos analog signal outputs from the filters can be increased in an amplifier for input to an analog-digital converter for conversion into digital electrical signals.

Echoes returning from a stationary target such as a settled bed level have the same frequency as the original transducer ultrasound pulse, whereas echoes from moving targets such as particles are shifted frequency equal to the Doppler shift frequency. The Doppler shift frequency is estimated by the equation $$f_d = (2vf_t/c) * \cos(\phi)$$

where $f_d$=Doppler shift frequency,
v=the velocity of particles,
$f_t$=transducer frequency,
c=speed of sound, and
$\phi$=the angle between the direction of the particles and the transducer ultrasound path. For example, if particles are flowing in a vertical direction, either up or down, then $\phi$=0 or 180° and cos ($\phi$)=1.

If an echo returns from a stationary target such as a settled bed level, the sin/cos channel analog signal outputs appear as in FIG. 3C. As shown in FIG. 3C, the frequency difference between the transducer ultrasound frequency and the echo frequency is approximately zero.

The polarity of the sin or cos analog signal depends upon the relationship between the phase of the sin/cos signal and the phase of the echo. For example, a unipolar amplitude signal from a clearly defined bed level, such as shown in FIG. 1A, is found by calculating the square root of the sum of the square of the sin channel plus the square of the cos channel.

Slowly moving isolated target echoes, such as echoes from a slowly moving bed level boundary, appear as in FIG. 3A. As also shown if FIG. 3A, the sin/cos analog output signals oscillate about the baseline at a frequency equal to the difference between the echo frequency and the transmitted pulse frequency. A unipolar analog signal as shown in FIG. 1B is obtained by taking the square root of the sum of the squares of the sin and cos analog signals.

Echoes from an unsettled cloud appear as in FIG. 3B. The oscillation frequency of the echoes about the baseline at any point along the transducer ultrasound path depends upon the frequency difference between the returned echoes and the transmitted pulse frequency at that point. Generally, sin/cos analog signal outputs for unsettled cloud layers are lower in amplitude than for settled bed layers.

Background noise echoes may interfere with the desired echoes from the unsettled cloud particles by introducing a spurious range phase. This spurious range phase can be identified by directing an ultrasonic pulse from the transducer away from the bottom of the tank to generate echoes which represent the background noise and for storage in the range phase memories. During transducer pulses, the spurious range phase data is read from the range phase cancellation memory and coherently subtracted from the echo signals to eliminate the spurious range phase data. The range phase cancellation memory requires periodic updating to account for varying settler conditions. The frequency of updating can be readily determined by the art skilled according to settler conditions.

Data collection variables and modes are established by operator input to the computer. The operator enters data for the settler depth, transducer repetition rate and the desired mode of operation, i.e., peak mode and moving particle mode, and the Doppler mode. If the Doppler mode is selected, the operator enters the number and depth location (s) of the Doppler samples. Conveniently, any of the peak method, moving particle method and the Doppler methods can be employed, as described below.

A computer summarizes operator input data and stores that data in a file on hard disk for ADC start, choice of image or Doppler modes, etc. At start of operation this memory information is read into the system logic for preselected depths of the transducer for the Doppler mode. All subsequent logic and timing signals for system operation are derived in the master oscillator block. These subsequent signals include ADC timing pulses, memory addresses and write pulses, as well as analog switch control signal.

As mentioned, settler conditions are transient. The bed level boundary therefore may not be in a satisfactory position for detection at the time of a given transducer pulse. Thus, at a specific moment, a distinct bed level perpendicular to the transducer ultrasound path may exist, but at the next instant, the bed level may become less distinct or is no longer perpendicular to the transducer ultrasound path. Advantageously, in the two image modes, echoes can be collected over several transducer pulses and stored in data acquisition memory. Data from the several transducer pulses increases the observation time of the bed level boundary, if it exists, and the probability of bed level detection.

Data in the data acquisition memory can be processed by three distinctly different methods as stated above. In the peak detection method, analog sine and cos signals are recalled from the memory on a transducer line-by-transducer line basis. As used herein, a transducer line is the collection of echoes returning from a single ultrasound pulse.

Advantageously, the peak method enables bed level detection even if only one transducer line in the data acquisition memory detected a bed level. In addition, if the settled bed level is detected by several transducer lines in the data acquisition memory, then the probability of detecting a bed level is increased. The resulting line shows the maximum echo point for each range increment on the transducer ultrasound path and presents echoes from the settled bed level to determine the bed level.

To initialize the system for use with the peak method, the initial value in each data point on the result lines for each of sin analog signal and cos analog signal is set to zero. As used herein, the result line is the line that presents the highest signal values at each depth within the settling tank from all recorded transducer lines in each sin and cos channel. For each transducer line, the signal value at each depth in the settling tank is compared to the value already present on the result line at that depth to the value at that corresponding depth from the sin and cos channels. Then, the greater of the two signal values is assigned to the result line. Of course, the first transducer line will be greater than the initialized values in the result line. This process is repeated over the number of transducer lines recorded in memory. The sin and cos channel result lines are equal to the depth by depth maximum value from the number of transducer lines.

The peak detection method provides a combined result line that is equal to the square root of the square of the sin channel data plus the square of the cos channel data on a point-by-point basis along each of the previous result lines. The bed level is found by locating the peak amplitude on the combined result line. When the bed level echo data has a random character, whether during the sum of the periods for transmitting the desired number of ultrasound pulses, i.e., the interrogation period, or fragmented across that same interrogation period, the peak method significantly increases the probability of bed level detection by selecting the peak value for each result line data point.

In the Peak Detection method, the bed level and the activity level of unsettled particles can be found by analyzing the resultant transducer line ultrasound data. Neural Network is the preferred method of analysis. Any of the available Neural Network software development packages can be used in our invention. By presenting resultant transducer lines of ultrasound data as the inputs and the corresponding measured realtime bed level and particle activity levels as the outputs, a neural network is constructed that "learns" from the measured data sets of inputs and outputs supplied to it. The resultant Neural Net developed model is then used in the control part of our invention.

The moving target method may be used when the peak detection method cannot find a settled bed level echo or when the bed level echoes are too near the background noise levels to be reliable. These conditions may exist when the particles may not be settling well, if at all, such as during an upset condition where one or more particle clouds can form. Within these clouds, the unsettled particles move with different speeds. Under these conditions, identification of the number of clouds, the particle activity within the clouds, and the size and position of the clouds is useful to describe the condition of the settler.

The moving target method recognizes that the moving particles change position between transducer pulses, thereby causing changes in the sine and cos analog signals. The moving target method estimates the particle motion by subtracting one transducer line of sin and cos analog signals from the next transducer line of data of sin and cos analog signals, and then taking the absolute value of that difference. The absolute values of differences are summed over the number of transducer lines. This sum represents an integrated score of particle activity from the transducer to the bottom of the settler. An integrated particle activity score through the depth of the settler is found by calculating the square root of the sum of square of the sin analog signal plus the square of the cos analog signal. Higher amplitudes indicate greater particle activity.

Clouds are found by the moving target method by identifying unsettled particles with an integrated (sum) activity score above a baseline value. The baseline value can be determined by plotting the integrated score of particle activity as a function of depth in the settler. The integrated particle activity scores for clouds are significantly higher than that for a column of liquid that is cloud-free. The number of occurrences where the integrated scores deviate from the baseline equates to the number of clouds present in the tank. Further, the locations of these deviations also indicate the locations of the cloud. Integrated activity scores thus can be used to identify the number of clouds, the particle activity within an individual cloud, and the extent of cloud formation to evaluate the status of the settler regardless of whether a peak method determined bed level is obtained. For example, a high activity score indicates a cloud with a high degree of individual particle activity. Large clouds present particle activity over a large range, while small clouds present particle activity over limited ranges. Cloud formation provides data for evaluating settler condition, and the need to adjust the amount and type of chemical additions, slurry additions, settler rake speed, etc. in the settler.

In certain situations, a bed level is not sufficiently compact for the peak method to detect. Such a bed level exists when there is a change in particle density or a change in particle motion. This type of bed level can be called a soft bed level. The integrated activity scores may be used to identify a soft bed level. When one exists and there is no overlapping cloud, the soft bed level will cause a sharper deviation from the baseline relative to a deviation caused by the cloud layer. When a cloud overlaps a bed, there will be no sharp deviation, but a bed level may be detected if the deviation caused by the cloud sharply or abruptly returns to the baseline. At the bed level, there is minimal particle movement. As a result, the integrated activity score is near the baseline.

In the Doppler mode, particle speed in ascending and descending directions is calculated at specific points along the path of the transducer's ultrasound path. According to the well known range equation above, a depth in the settler is selected and the time $T_o$ at which the ultrasound signal is transmitted is recorded. At a predetermined time $T_f$, the frequency and amplitude of particle echoes is recorded. Time $T_f$ is preset to correspond to a particular depth in the slurry based on the speed of sound in the liquid. By varying $T_f$ the settling rate of particles at various distances from the transducer face into the tank can be monitored. Measurements at different depths can be obtained under computer control to construct settling rate profiles as a function of time by FFT.

In the Doppler mode, the system of the invention can accommodate a number of sample points, such as $P_1$ and $P_2$ in FIG. 2A. Conveniently, eight sampling points may be used. Only one data point in the sin and cos channels need be taken at each sample point for each line of transducer data. After data acquisition is completed, the sin and cos analog signal for each sample point are retrieved from the data acquisition memory. These sin and cos analog data are analyzed using Fast Fourier Transform (FFT) or other frequency spectral techniques or spectral analyzer algorithm, such as autoregressive techniques.

The sampling time period or interrogation period required for use with the Doppler method is determined by the minimum particle velocity to be detected. In a settler, minimum particle velocities are on the order of 1–2 inches/minute. The sampling time period therefore is $(1/f_d)$, where $f_d$ is the Doppler frequency corresponding to the minimum particle velocity. Low velocities correspond to low frequencies in the FFT. Observation times in the order of a 10 seconds may be required to achieve this degree of resolution of particle speed by FFT. The minimum transducer repetition frequency, however, is determined by the maximum particle velocity expected. For example, using a 500 kHz transducer and a maximum particle velocity of 0.5 ft/sec, the Doppler frequency is about 152 Hz, requiring a transducer repetition frequency of at least 304 Hz.

In the Doppler mode, the range for a Doppler sample should be within the transducer repetition frequency range. In addition, limited length waveguide or a 'quiet box' can be employed. The waveguide serves as a chamber where the settler circulating currents introduced by the rotating rake and the inflow from the center well are significantly attenuated. Without the waveguide, the circulating currents cause the particles to move in directions other than the vertical, making the Doppler speed and direction information difficult to interpret. Doppler information from a waveguide corresponds closely with the sedimentation rates measured manually using a graduated cylinder outside the setter environment.

In an alternative embodiment, the settled bed level and the particle clouds may be measured at two or more sites within a settling tank by positioning additional transducers further from the center well of the tank than the first, primary transducer. Multiple transducers may be used to maintain a high signal to noise ratio in bed level echoes to overcome problems of reduced signal to noise ratio in bed level echoes due to bubbles. If bubbles adhere to a sufficiently large area of the transducer face, the transducer will not operate efficiently, if at all. If bubbles accumulate on either of the transducers, the bubbles can be removed by a wiper that passes under the transducer. Generation of bubbles can be a significant problem in an aluminum clarifier. Bubbles may arise when liquids are heated to temperatures near or above boiling. Bubbles also can arise when the liquid slurry is released from a high pressure source into a settler. A secondary transducer normally is free from bubbles unless the entire clarifier contains boiling liquid.

As stated above, a waveguide or a "quiet box" may be positioned in a settler. The waveguide including the transducer extends into the settler suspension. The waveguide attenuates the effects of random circulating currents which may be present in the settler to enhance measurement of the downward movement of the settling particles.

The waveguide can be a cylinder with slots therein to allow a liquid slurry to enter the waveguide. Waveguides are made from materials capable of withstanding temperatures above 100° C. and corrosive liquids and which do not bend under currents which might misdirect the ultrasound beam.

The waveguide causes the transducer beam to approach a plane wave that remains essentially constant over the length of the waveguide to reduce beam spreading to minimize any significant decrease of echo amplitude and detection reliability. The waveguide also attenuates circulating currents present in the settler. Attenuation of circulating currents provides particle vertical settling rates which correlate well with rates obtained manually with a suspension in a graduated cylinder outside the settler and a stopwatch.

Positioning a transducer at the top end of the waveguide effectively increases the diameter of transducer to that of the waveguide, and also effectively positions the transducer closer to the bed level particle interface by a distance equal to the length of the waveguide. A further advantage of positioning a transducer at the end of a waveguide is that measurement of sample volume required to obtain settling rate data can be taken electronically at various positions in the waveguide.

As mentioned, settling process conditions within a tank can be transient. It therefore is important to avoid upset conditions which may disrupt the settling process conditions. Advantageously, the particle settling rate and the position of the settled bed level obtained by the system and method of the invention can be employed to control the rate of addition of chemical additives and particle slurry to the tank.

Figure 5:
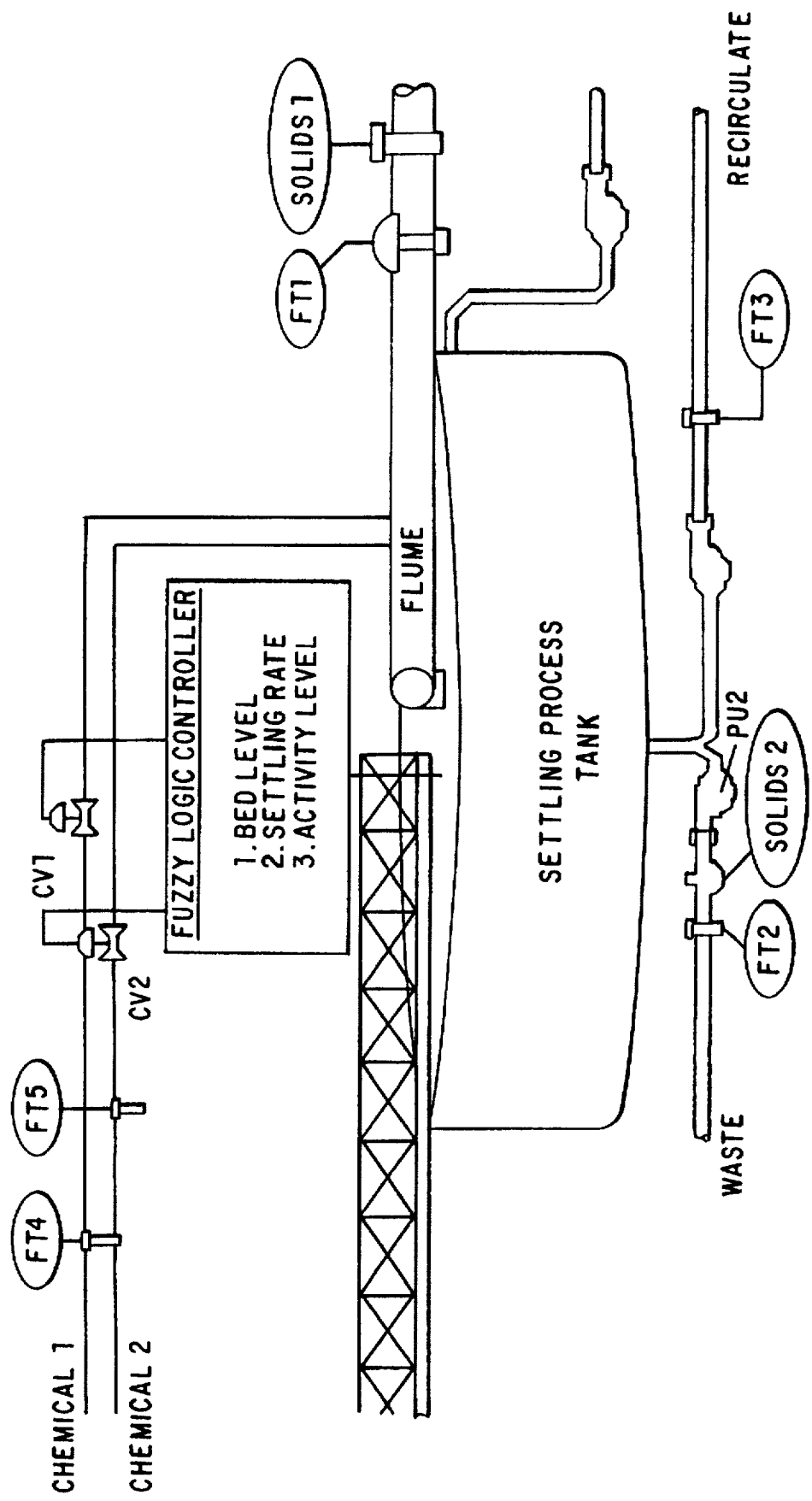
FIG. 5 is a schematic of a bed level control process.

As shown in FIG. 5, the bed level and settling rate can used to control the rate of addition of chemicals 1 and 2 via valves CV1 and CV2, respectively, to a slurry of solids 1 added to settling process tank via the flume to cause solids to precipitate and to thereby recover substantially clear liquid. As shown in FIG. 5, precipitated waste solids are drawn from the settling tank via pump PU2 and residual liquid is recirculated to the slurry.

The resultant neural network software developed model takes the real-time ultrasound measurements and calculates the corresponding bed level and activity level inputs to a Fuzzy Logic controller. The Fuzzy Logic controller calculates the outputs to valves CV1 and CV2 (FIG. 5), controlling the addition of chemicals 1 and 2 to give the desired bed level and activity level set points to control the dynamic conditions of the settler. This Fuzzy Logic controller can be based on any of the commercially available Fuzzy Logic software control packages, with, for example, the neural net model presenting inputs to the Fuzzy Logic controller, with object codes for both the Fuzzy Logic and Neural Net programmed in C, FORTRAN, or any other transportable coding system. The Fuzzy Logic controller consists of a series of rules that governs the addition of chemicals 1 and 2, and any other additional chemicals, and/or other control parameters of the settler, such as pump PU2 of FIG. 5, controlling the underflow pump out rate, thus controlling the settler set points.

We claim:

1. A method for locating the bed level of settled particles within a slurry comprising,
    transmitting ultrasonic sound waves into a slurry of particles to generate echoes from said particles,
    generating electric signals from said echoes,
    processing said electrical signals to identify a bed level of settled particles by peak method comprising the steps of:
        dividing the signals from said echoes into sine and cosine channels;
        multiplying the signals in the sine channel by a sine signal of the same frequency as the ultrasonic sound waves;
        multiplying the signals in the cosine channel by a cosine signal having the same frequency as the ultrasonic sound waves;
        converting the signals in each of the sine and cosine channels to digital signals;
        storing the digital signals according to transducer lines in memory;
        assigning the highest echo amplitude from all the transducer lines as a function of depth to one or more result lines for each channel;
        constructing a combined result line from one or more result lines, and
        locating the bed level by identifying the highest value on the combined result line by converting said highest echo amplitudes into an input data file format, processing the input data file by a neural network to provide outputs and identifying said outputs as bed level and activity level signals.

2. The method of claim 1 wherein the bed level and activity level signals are inputted to Fuzzy Logic controller device to generate one or more additional output signals.

3. The method of claim 2 wherein said additional output signals are inputted to one or more control devices to control the addition of chemicals to said slurry.

4. A system for determining the bed level of settled particles in a slurry comprising,
    means for sending ultrasound signals into a slurry,
    means for receiving echoes caused by the reflection of the ultrasound signals from solid particles in the slurry,
    means for converting said echoes to a first set of analog electrical signals,
    means for multiplying said second analog signals to a means for converting said analog signals to digital signals, a data acquisition memory for storing the digital signals for numerical processing by peak method or moving target method thereby providing a combined result line, means for converting highest echo amplitudes of the combined result line into an input data file format, neural network means for processing said input data file to provide outputs, and means for identifying said outputs as bed level and activity level signals.

5. A system according to claim 4 further comprising, a Fuzzy Logic controller device capable of receiving said bed level and activity level signals and generating one or more additional output signals.

6. A system according to claim 5 comprising one or more control devices capable of receiving said additional output signals and controlling the addition of chemicals to said slurry.

* * * * *

UNITED STATES PATENT AND TRADEMARK OFFICE
CERTIFICATE OF CORRRECTION

PATENT NO. : 5,789,676
DATED : August 4, 1998
INVENTOR(S) : Charles Robert Fay, et al.

It is certified that error appears in the above-identified patent and that said Letters Patent is hereby corrected as shown below:  On the title page: Item [56]

U. S. PATENT DOCUMENTS

| EXAMINER INITIAL | PATENT NUMBER | ISSUE DATE | PATENTEE | CLASS | SUBCLASS | FILING DATE IF APPROPRIATE |
|---|---|---|---|---|---|---|
|  | 4 9 8 0 8 6 8 | 12-25-1990 | Teel |  |  |  |
|  | 5 6 3 5 6 3 2 | 06-03-1997 | Fay et al. |  |  |  |
|  |  |  |  |  |  |  |

FOREIGN PATENT OR PUBLISHED FOREIGN PATENT APPLICATION

| | | DOCUMENT NUMBER | PUBLICATION DATE | COUNTRY OR PATENT OFFICE | CLASS | SUBCLASS | TRANSLATION YES | NO |
|---|---|---|---|---|---|---|---|---|
|  |  | GB 2 2 5 6 049 A | 11-25-1992 | United Kingdom |  |  |  |  |
|  |  |  |  |  |  |  |  |  |
|  |  |  |  |  |  |  |  |  |
|  |  |  |  |  |  |  |  |  |

OTHER DOCUMENTS (Including Author, Title, Date, Pertinent Pages, Etc.)

F.J. Thomson, Medical & Biological Engineering and Computing March 1978, pp 135-146

Broadband pulsed Doppler ultrasonic system for the noninvasive measurement of blood velocity Signed and Sealed this Ninth Day of November, 1999

Attest:

Q. TODD DICKINSON

*Attesting Officer*      *Acting Commissioner of Patents and Trademarks*